(12) United States Patent
Gerrans et al.

(10) Patent No.: US 9,936,872 B2
(45) Date of Patent: Apr. 10, 2018

(54) VISUALIZATION OF EYE ANATOMY

(71) Applicants: Lawrence J. Gerrans, San Anselmo, CA (US); Charles N. Wang, Santa Clara, CA (US)

(72) Inventors: Lawrence J. Gerrans, San Anselmo, CA (US); Charles N. Wang, Santa Clara, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 0 days.

(21) Appl. No.: 14/582,716

(22) Filed: Dec. 24, 2014

(65) Prior Publication Data

US 2015/0173613 A1   Jun. 25, 2015

Related U.S. Application Data

(60) Provisional application No. 61/920,610, filed on Dec. 24, 2013.

(51) Int. Cl.
*A61B 3/14* (2006.01)
*A61B 3/00* (2006.01)
*A61B 3/10* (2006.01)
*A61B 3/113* (2006.01)

(52) U.S. Cl.
CPC .............. *A61B 3/14* (2013.01); *A61B 3/113* (2013.01)

(58) Field of Classification Search
CPC .............. A61B 3/00; A61B 3/10; A61B 3/02
USPC ......... 351/200, 205–206, 210, 221–223, 246
See application file for complete search history.

(56) References Cited

U.S. PATENT DOCUMENTS

| | | | | |
|---|---|---|---|---|
| 4,978,213 A | * | 12/1990 | El Hage | A61B 3/107 351/212 |
| 5,450,144 A | * | 9/1995 | Ben Nun | A61B 3/12 351/205 |
| 6,992,775 B2 | | 1/2006 | Soliz et al. | |
| 7,331,669 B2 | | 2/2008 | Elsner | |
| 8,226,601 B2 | | 7/2012 | Gunday et al. | |
| 8,363,783 B2 | | 1/2013 | Gertner et al. | |
| 8,540,667 B2 | | 9/2013 | Gerrans et al. | |
| 8,597,239 B2 | | 12/2013 | Gerrans et al. | |
| 2006/0077343 A1 | | 4/2006 | Sekiguchi | |

(Continued)

FOREIGN PATENT DOCUMENTS

WO   2010131944 A2   11/2010
WO   2012088424 A1   6/2012

OTHER PUBLICATIONS

International Search Report and Written Opinion of the International Searching Authority Application No. PCT/US2014/072184 Completed: Mar. 2, 2015; dated Apr. 16, 2015 10 pages.

*Primary Examiner* — Dawayne A Pinkney
(74) *Attorney, Agent, or Firm* — Forge IP, PLLC

(57) ABSTRACT

A system for visualization of eye anatomy includes at least one camera having a view vector along a first axis when in a first position, a housing to which the at least one camera is coupled, wherein the housing is configured to engage an eye of a patient such that the at least one camera is positioned adjacent the eye, and an actuator that moves the at least one camera from the first position to a second position, wherein the at least one camera, when in the second position, has a view vector along a second axis that is offset from the first axis.

31 Claims, 10 Drawing Sheets

(56) References Cited

U.S. PATENT DOCUMENTS

| | | | |
|---|---|---|---|
| 2007/0159600 A1* | 7/2007 | Gil | A61B 3/0008 351/221 |
| 2007/0291226 A1* | 12/2007 | Fujii | A61B 3/0091 351/210 |
| 2009/0190093 A1 | 7/2009 | Tanassi et al. | |
| 2011/0205491 A1* | 8/2011 | Koiwa | A61B 3/18 351/206 |
| 2012/0101371 A1* | 4/2012 | Verdooner | A61B 3/12 600/425 |
| 2012/0127427 A1 | 5/2012 | Guo et al. | |
| 2012/0249959 A1 | 10/2012 | You et al. | |
| 2013/0102895 A1 | 4/2013 | Gooding et al. | |
| 2013/0215383 A1* | 8/2013 | Siminou | A61B 3/14 351/206 |

* cited by examiner

VISUALIZATION OF EYE ANATOMY

FIELD OF THE INVENTION

The present invention relates to systems and methods for visualizing eye anatomy for diagnostic and therapeutic purposes. More specifically, the present invention relates to a system and method of visualizing eye anatomy by using a contact device together with a small articulatable imager to provide a wide angle field of view.

BACKGROUND OF THE INVENTION

Diabetic retinopathy is a disease characterized by damages to retina caused by complications of diabetes. The retina is a nerve layer that lines the back of the human eye. It is the part of the eye that captures the visual images and sends the images to the brain.

Diabetic retinopathy can be a serious condition and can often lead to poor vision or even blindness if not treated timely. Diabetic retinopathy is typically caused by changes in retinal blood vessels, which are induced by high blood sugar levels in a diabetic patient. These changes lead to improper formation of the blood-retinal barrier and make the retinal blood vessels become weak and more permeable.

A problem with diagnosing diabetic retinopathy is that it typically begins at the periphery of the retina, which is difficult to see, and then works its way towards the center of the retina, at which point it can be too late to treat and blindness can set in. Physicians often use microscope-like devices with or without an attached camera that have a fixed field of view (typically between 20-50 degrees) to try to diagnose diabetic retinopathy. However, such examination sometimes does not reveal signs of retinopathy present at the periphery of the retina because of the limited field of view of these cameras. Thus, in order to see the periphery of the retina, it is desirable to increase the field of view when diagnosing retinopathy. It is also desirable to expand the number of spectrums and wavelengths to identify aspects of eye anatomy and pathology not found in the visible spectrum and associated wavelengths currently being employed.

There are few newer technologies that have been developed for more accurately diagnosing diabetic retinopathy. One such technology is a coherence tomography technology, as disclosed, for example, in US 2012/0127427 by Guo et al. This is an imaging technology similar to regular ultrasound. It utilizes an optical beam that is directed at eye tissue and a small portion of light that reflects from sub-surface structures is collected to re-create a 3D image of the retina. While this technique has many advantages, the equipment is very complex and expensive, making it not easily accessible to all patients and clinics. Further, a patient's pupil needs to be dilated during the procedure, which makes it more uncomfortable for the patient.

Another newer type of an imaging technique is a confocal scanning laser ophthalmoscope, which creates an image of the retina with a high degree of spatial sensitivity. Again, while this technique has many advantages, the required equipment is typically extremely cumbersome and expensive.

Yet another type of a retina imaging device is described in WO 2012/088424 by Busuioc et al. The device includes a camera having a body and at least one optical sensor provided on the body and configured to receive light directly from a lens of an eye. The optical sensor can be positioned closer or further away from the eye to focus the camera. While this device is rather simple and inexpensive, it still suffers from a number of disadvantages. For example, because the camera remains in the same position relative the surface of the eye, still only a limited angle of view of the eye anatomy can be captured. Additionally, because the camera does not utilize a lens, the quality of image of the eye anatomy obtained by the camera is fairly low.

Therefore, while various newer optical imaging techniques provide improved imaging capabilities, there is still a need for a simpler and more affordable device and method that allows for a simplified but accurate imaging of a person's retina to detect symptoms of diabetic retinopathy in addition to other eye diseases.

Additionally, it is possible that diseases of the body can be detected by finding trace elements of their existence by visualizing the anatomy of the eye. Alzheimer's disease is a neurodegenerative disease characterized by an increase of tiny inclusions in the nerve tissue, called plaques. These plaques are found between the dying cells in the brain from the build-up of a protein called beta-amyloid. Beta amyloid protein has been found to aggregate in the lens of the eye. Accordingly, the ability to detect and measure beta amyloid aggregates in the eye creates an opportunity to detect and diagnose the onset of Alzheimer's disease.

Conformational diseases, which include more than 40 disorders, are typically caused by the accumulation of unfolded or misfolded proteins. Improper protein folding or a so-called misfolding, together with accrual of unfolded proteins, leads to the formation of disordered (amorphous) or ordered (amyloid fibril) aggregates. Characteristic late or episodic onset of the conformational diseases is caused by the gradual accumulation of protein aggregates and the acceleration of their formation by stress. The best studied conformational diseases are neurodegenerative diseases and amyloidosis, which are accompanied by the deposition of specific aggregation-prone proteins or protein fragments and formation of insoluble fibrils. Amyloidogenic protein accumulation often occurs in the brain tissues. For example, Alzheimer's disease is associated with deposition of amyloid-beta and Tau, scrapie and bovine spongiform encephalopathy is associated with accumulation of prion protein, and Parkinson's disease is associated with deposition of alpha-synuclein. The accumulation of unfolded or misfolded proteins, which leads to pathology, also takes place in a variety of other organs and tissues, including different parts of the eye. Some of the best studied ocular conformational diseases include cataract in the lens and retinitis pigmentosa in the retina. However, deposition and accumulation of unfolded or misfolded proteins also occurs in other parts of the eye causing various disorders. Ocular manifestation of systemic amyloidosis can also cause deposition of amyloidogenic proteins in different ocular tissues.

What is desired, therefore, is an imaging device that is simpler and more affordable than known imaging devices that allows for a simplified but accurate imaging of a person's eye anatomy to detect symptoms of various eye diseases. What is also desired is an imaging device that utilizes a contact device together with a small articulatable imager with one or more spectrums combined with one or more wavelengths to visualize eye anatomy, as well as various biological material present in the eye and to detect its structures and molecular mechanisms underlying its involvement in diseases.

SUMMARY OF THE INVENTION

The system and method of the present invention provides a number of advantages over the known optical imaging systems. On one hand, it is inexpensive and easy to use, thereby not requiring highly specialized training of physicians and making it more affordable to clinicians and patients. On the other hand, the device of the present invention allows an examining physician to obtain a much wider field of view as compared to conventional imaging techniques, thereby making the early diagnosis of diabetic retinopathy and other eye conditions and diseases more likely. In addition, the system and method provides clinicians the ability to use one or more spectrums and one or more wavelengths to visualize the anatomy of the eye.

In order to overcome the deficiencies of the prior art and to achieve at least some of the objects and advantages listed, the invention comprises a system for visualization of eye anatomy, including at least one camera having a view vector along a first axis when in a first position, a housing to which the at least one camera is coupled, wherein the housing is configured to engage an eye of a patient such that the at least one camera is positioned adjacent the eye, and an actuator that moves the at least one camera from the first position to a second position, wherein the at least one camera, when in the second position, has a view vector along a second axis that is offset from the first axis.

In some embodiments, the second axis is angularly offset from the first axis. In other embodiments, the second axis is substantially parallel to the first axis.

In certain embodiments, the system further includes a processor that processes image data captured by the at least one camera.

In some embodiments, the at least one camera includes a plurality of cameras positioned adjacent the same eye of the patient. In certain of these embodiments, each of the plurality of cameras moves separately from the other cameras. In additional of these embodiments, the plurality of cameras move together as a unit.

In some cases, the system further includes at least one illumination device positioned adjacent the at least one camera. In certain of these embodiments, the at least one illumination device includes a light source having at least one of a visible, ultraviolet, infrared and near infrared spectrum.

In certain embodiments, the system further includes a storage device that stores image data captured by the at least one camera.

In some embodiments, the system also includes a 2-D or 3-D display coupled to the at least one camera for displaying image data captured by the camera.

In certain embodiments, the actuator moves the at least one camera from the first position to a third position, wherein the camera has a view vector along the first axis when in the third position.

In some cases, the at least one camera captures a field of view of at least 180 degrees when moved from the first position to the second position.

In certain embodiments, the housing includes a suction member for attachment to the patient's eye.

In some embodiments, the system further includes a vacuum source that supplies vacuum to the housing to assist in attachment of the housing to the patient's eye.

In certain advantageous embodiments, the at least one camera includes at least one lens and at least one imaging sensor. In some of these embodiments, the imaging sensor comprises a CMOS sensor.

In some embodiments, the system further includes a tracking system configured to track movement of the eye. In additional embodiments, the system further includes a tracking system configured to track movement of at least one structure and/or material within the eye.

A method of visualization of eye anatomy is also provided, including the steps of engaging a patient's eye with a housing having at least one camera coupled thereto such that said the at least one camera is positioned adjacent to an eye of the patient, wherein the at least one camera has a view vector along a first axis when in a first position, and moving the at least one camera to a second position, wherein the at least one camera, when in the second position, has a view vector along a second axis that is offset from the first axis.

In some embodiments, the method further includes the step of capturing image data with the at least one camera.

In certain embodiments, the second axis is angularly offset from the first axis. In additional embodiments, the second axis is substantially parallel to the first axis.

In some embodiments, the at least one camera comprises a plurality of cameras positioned adjacent the same eye of the patient. In certain of these embodiments, the step of moving said the at least one camera comprises moving each of the plurality of cameras separately from the other cameras. In additional of these embodiments, the step of moving the at least one camera comprises moving the plurality of cameras together as a unit.

In some cases, the method also includes the step of storing image data captured by the at least one camera on a storage device.

In certain embodiments, the method further includes the step of displaying to a user image data captured by the at least one camera. In some of these embodiments, the image data displayed to the user is an image comprising two or more images captured by the at least one camera, wherein two or more images are at least partially overlapping to create the displayed image.

In some cases, the method also includes the step of transmitting image data captured by the at least one camera to a remote location for display to a user and/or storage.

In certain embodiments, the method further includes the step of illuminating the eye via at least one illumination device positioned adjacent the at least one camera.

In some embodiments, the method also includes the step of moving the at least one camera from the first position to a third position, wherein the camera has a view vector along the first axis when in the third position.

In certain embodiments, the step of measuring a diameter of an iris and adjusting the position of said at least one camera based at least in part on the measured diameter.

In some embodiments, the step of tracking movement of the eye and adjusting positioning of the at least one camera based on the movement of the eye. In additional embodiments, the step of tracking movement of at least one structure and/or material within the eye and adjusting positioning of said at least one camera based on the movement of the at least one structure and/or material within the eye.

In certain embodiments, the step of engaging the patient's eye with the housing includes engaging the patient's eye with a suction member provided in the housing. In additional embodiments, the step of engaging the patient's eye with the housing includes supplying vacuum to the housing via a vacuum source connected to the housing to assist in attachment of the housing to the patient's eye.

Other objects of the invention and its particular features and advantages will become more apparent from consideration of the following drawings and accompanying detailed description.

DETAILED DESCRIPTION OF THE INVENTION

Figure 1:
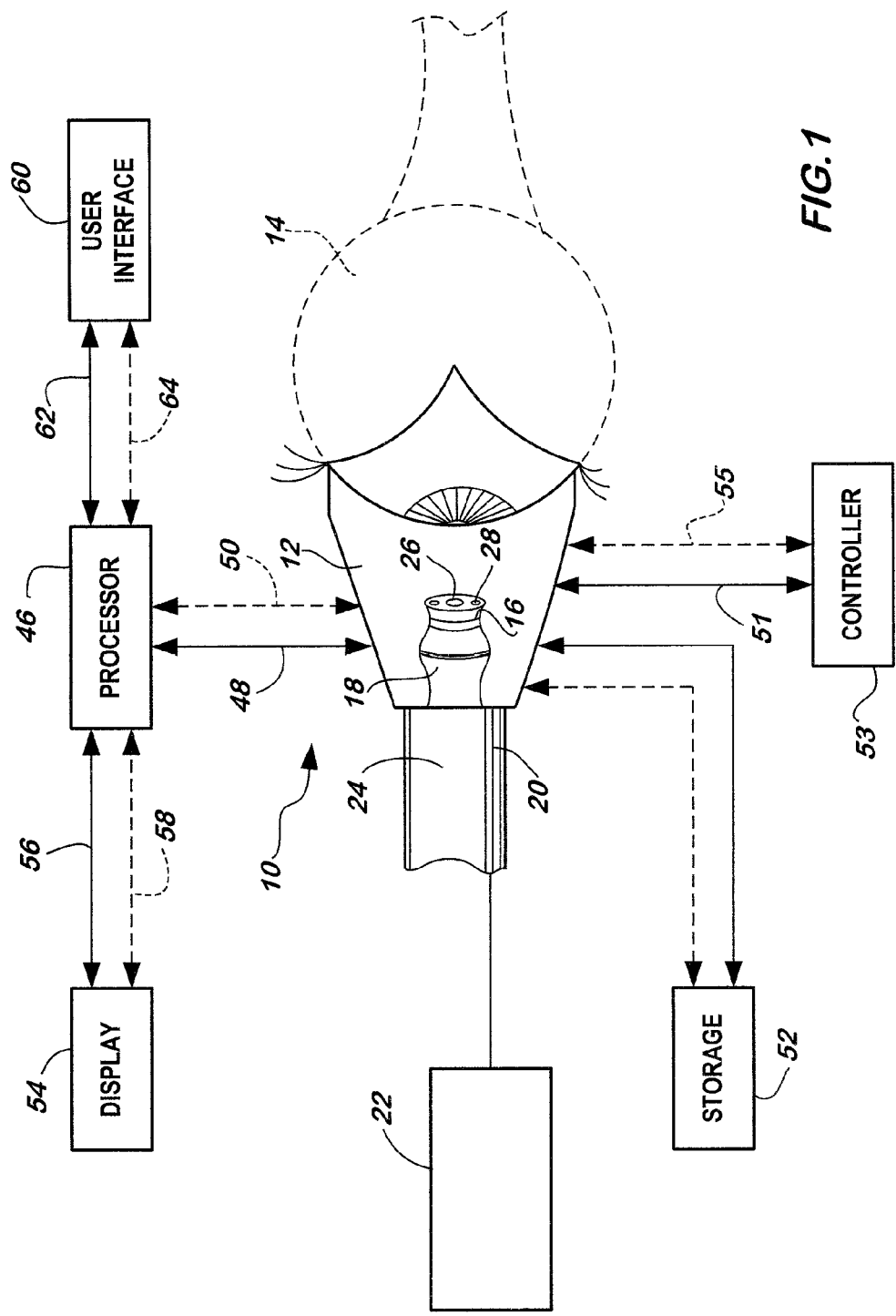
FIG. 1 is a schematic view of a system for visualization of eye anatomy in accordance with the present invention positioned adjacent a person's eye.

The basic components of one exemplary embodiment of a system for visualization of eye anatomy in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system of the present invention utilizes a very small imaging device in combination with a vacuum-coupled contact device to image a person's eye anatomy. The imager is manually or mechanically articulatable by the physician to obtain a wide view angle of at least 180 degrees, thereby allowing examination of the periphery of the retina to detect early signs of diabetic retinopathy. It is understood that the system may also be used to image the eye anatomy for any other therapeutic and/or diagnostic purpose.

In some cases, it is useful to detect, observe and analyze various tissue deposits in the eye to diagnose and treat various diseases of the eye and other organs. For example, depositions of lipids, crystals, proteins and other artifacts in the eye may provide useful information regarding various diseases of the body. The ability to detect, measure and analyze these deposits by visualizing the anatomy of the eye creates an opportunity to detect and diagnose various diseases of the eye and other organs and systems.

The present invention can identify changes in the geography of the eye, including atrophy, emaciation, and swelling. Furthermore, the present invention allows for detection and analysis of various conditions of the eye, such as, for example, hydration, innervations, inflammation, circulation, nerve conduction, etc. Each of these conditions is typically caused by one or more diseases, and being able to visualize and measure these conditions in the eye provides very useful information regarding the cause, extent and diagnosis of various diseases of the body.

In an exemplary embodiment of the present invention shown in FIG. 1, the system for visualization of eye anatomy (10) includes a housing (12) configured to engage an eye (14) of a patient. In some advantageous embodiments, the housing (12) is a cup-like member having a front portion that engages the patient's sclera, which is the white portion of the eye. The housing (12) includes a fluid/vacuum lumen (20) coupled to an external fluid/vacuum supplying device (22), such as a pump or a syringe. The vacuum assist in attachment of the housing (12) to the patient's eye (14). Additionally, the housing preferably includes a guide member (24), such as a handle or the like, to assist the physician in positioning the housing over the patient's eye.

In other advantageous embodiments of the invention, the housing (12) is a conventional scleral lens. This type of lens rests on the sclera and creates a tear-filled vault over the cornea. The lens can be made with various types of suitable sterile material, such as, for example, an oxygen permeable polymer, and is typically disposable after each use. In order to secure the lens to the patient's eye, a light vacuum-assisted suction is used hold the lens in appropriate position over the eye.

It is understood, however, that other types of housing may be used in accordance with the present invention. Also, other types of positioning mechanisms may be used, such as, for example, attaching a member holding the housing (12) to a patient's face or head. For example, in some embodiments, the housing (12) for each eye may be mounted on a piece of eye wear, which is then positioned on the person's head while each of the housings (12) engages the person's eye. It is understood that any other configuration of the holding member may be used in accordance with the present invention.

The system (10) further includes at least one imaging device (16) coupled to the housing (12). The imaging device (16) comprises at least one camera (26) and at least one illumination device (28) positioned adjacent the camera to illuminate tissue inside the eye to facilitate better imaging of the eye anatomy.

The camera (26) may comprise any imaging device suitable for viewing the target area, such as a coherent fiber bundle or appropriate optical element and lens assembly in conjunction with an imaging sensor (e.g., CMOS, CCD), having a sufficiently small outer diameter, preferably about 0.75 mm-2.5 mm, and more preferably about 1 mm or less, such that it fits inside the housing (12) that engages the eye. For example, the system of the present invention may utilize a proprietary camera, such as is described in U.S. Pat. No. 8,226,601 to Gunday et al. and U.S. Pat. No. 8,597,239 and U.S. Pat. No. 8,540,667 to Gerrans et al., the disclosure of which is incorporated herein in its entirety.

Figure 2A:
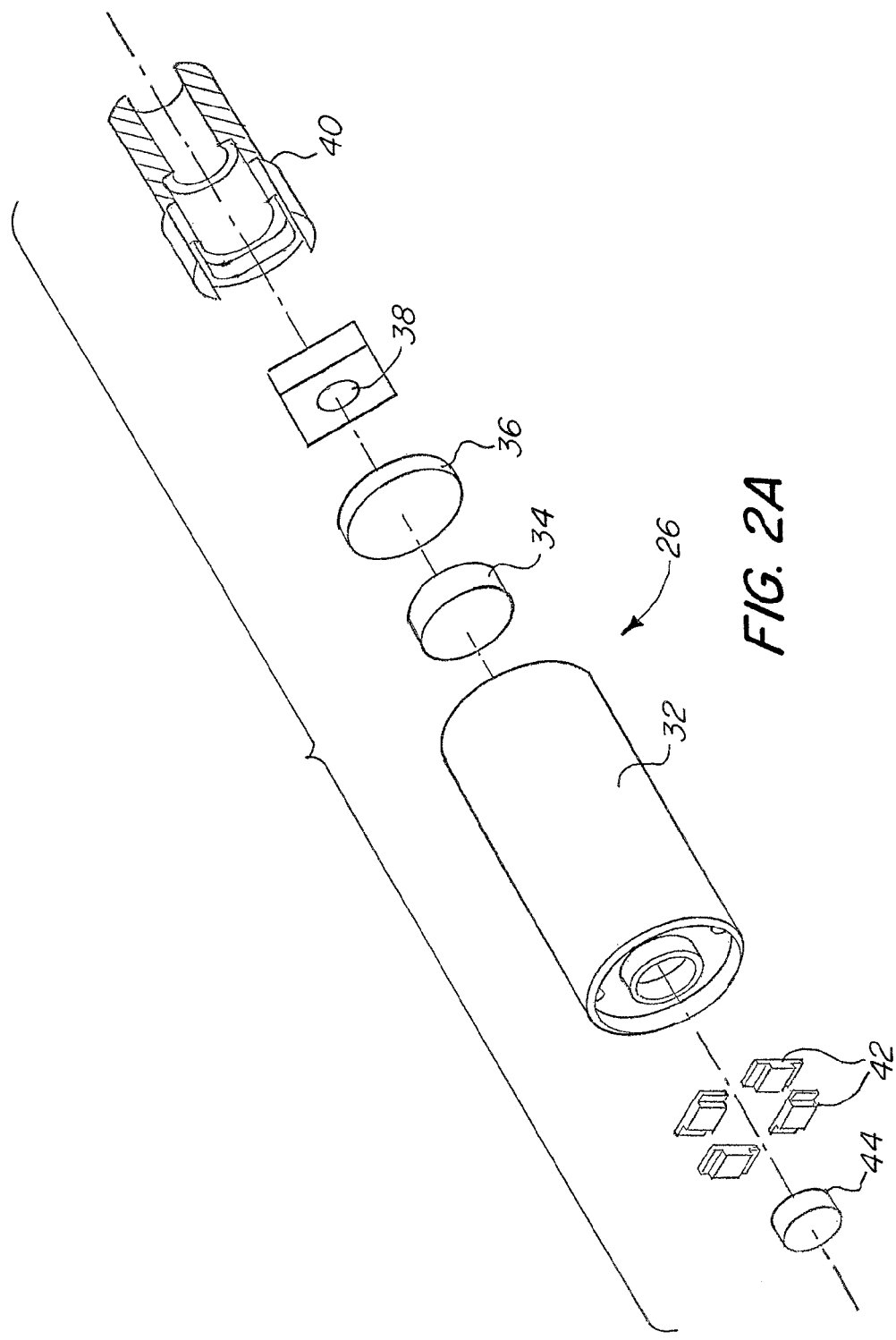
FIGS. 2A and 2B are exploded perspective views of a camera used in the system for visualization of eye anatomy of FIG. 1.
Figure 2B:
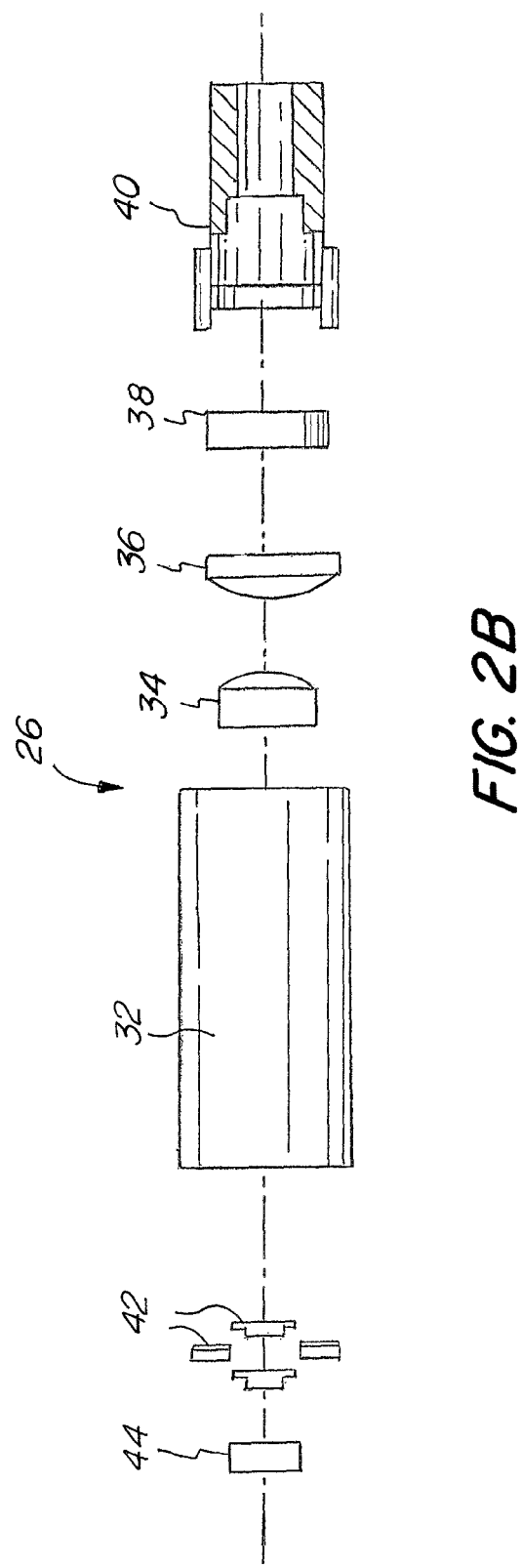
Figure 3A:
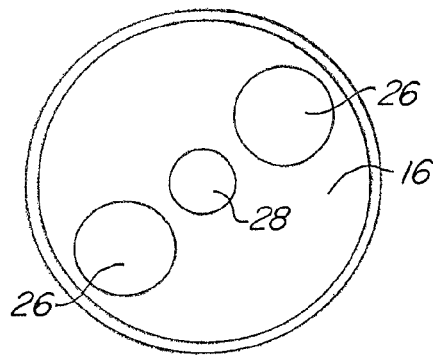
FIGS. 3A-3F are front views of various configurations of cameras and illumination devices of the system for visualization of eye anatomy of FIG. 1.
Figure 3B:
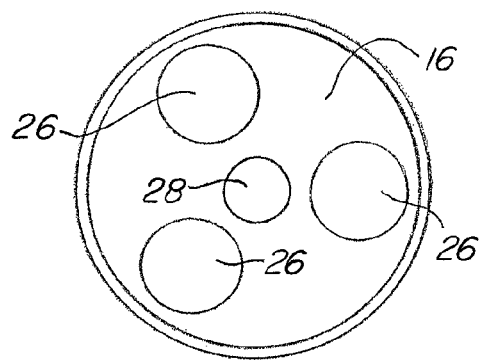
Figure 3C:
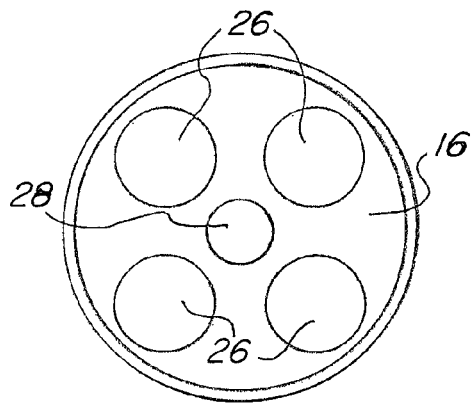
Figure 3D:
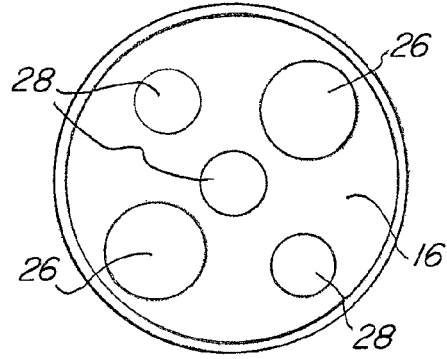
Figure 3E:
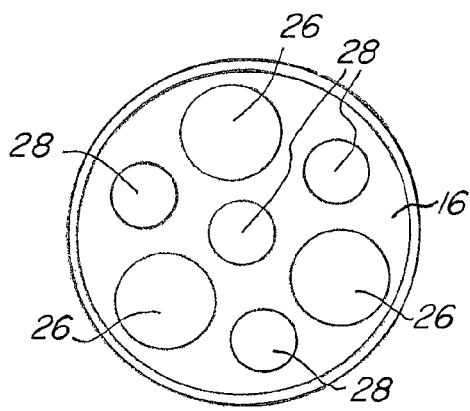
Figure 3F:
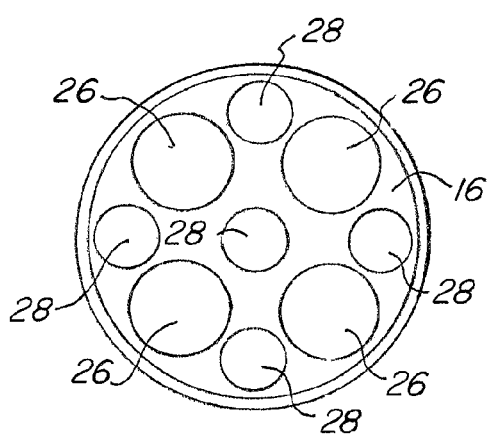

One advantageous camera embodiment is illustrated in FIGS. 2A and 2B. The camera (26) includes a camera housing (32) that houses all camera components. The housing (32) is made with any suitable material, such as plastic or metal, and has any desired shape and size. The camera also includes one or more lens positioned in the housing. In the embodiment shown in these figures, the camera includes two plano-convex lenses (34) and (36) positioned opposite of each other such that the convex sides of the lenses are facing each other. It is understood that any other lens type and arrangement may be used in accordance with the present invention, as desired.

The camera (26) further includes an imaging sensor (38) positioned proximally from the lens (34) and (36). Any type of imaging sensor may be used. The imaging sensor (38) is coupled a sensor mount (40) to fixate the sensor inside the housing. In one advantageous embodiment, a CMOS sensor is used. The housing (32) also has one or more illumination devices (42), e.g. LEDs, lasers, and/or fiber optic cables, positioned distally from the lens. It is understood than other types of illumination devices may be used. The illumination devices emit various types of light, depending on desired application. For example, the illumination devices may emit ambient light, visible spectrum light, ultraviolet light, infrared light, near infrared light, etc. A distal end of the housing (32) has a pupil relay system (44) that seals the distal end of the housing to protect the camera components positioned in the housing.

It is understood that the camera design illustrated in FIGS. 2A and 2B is only exemplary and that any other camera design may be used with the system of the present invention. The camera is coupled to an actuator that enables a linear or rotational movement of the camera, as described in more detail below, to provide a larger angle of view.

Any desirable configurations of the cameras (26) and the illumination devices (28) may be provided in accordance with the present invention. Some exemplary configurations are shown in FIGS. 3A-3F. In the embodiments illustrated in these figures, two, three, or four cameras (26) may be used to image a single eye. The cameras (26) may be positioned in any desirable configuration, such as in line or in a shape of a triangle or a square. One, two, three, four or five illumination devices (28) may be used together with any number and configuration of the cameras (26), and the illumination devices (28) may be have any desirable orientation with respect to the cameras. It is noted that the numbers and configurations of the cameras and illumination devices shown in these figures are only exemplary, and that any other number and/or arrangement of the cameras and illumination devices may be used in accordance with the present invention.

As described above, the system of the present invention allows examination of the eye anatomy using light of various spectrums and various wavelengths. This allows for detection, visualization and characterization of various tissues, structures, and molecular compounds that may be present in the eye, which in turn lead to diagnosis of various eye and body diseases. This is due to the fact that various tissues and structures that may be present in the eye absorb and/or deflect light of various spectrum and/or wavelengths in different ways. Analysis of the light scattering thereby provides information about particular tissues and structures present in the eye. The system of the present invention also allows for detection and characterization of changes in eye anatomy over time, which may be caused by various diseases. The system is capable of measuring color saturation of the light emitted onto the target tissues and also measures scattering of light deflected from the target tissues in the eye.

As noted above, the system of the present invention may utilize a plurality of illumination devices or light sources. In some embodiments, all of the light sources emit light of the same spectrum/wavelength. In additional embodiments, each of the plurality of light sources emits light of a different spectrum/wavelength than the light emitted by other light sources. This allows for detection and characterization of various structures and conditions inside the eye, as described above.

In some advantageous embodiments, the system of the present invention utilizes a continuous wave/stream of light. In other advantageous embodiments, the system uses a pulsed light, wherein the light emitting devices positioned on the system adjacent the cameras emit pulses of light at a desired frequency. The cameras may capture image data after each pulse of light, or at particular intervals after a certain number of light pulses. In further advantageous embodiments, the same light sources may emit light in both continuous wave and pulsed waves, as desired, and/or some of the light sources may emit light continuously and other light sources may emit light in pulsed waves.

Figure 6A:
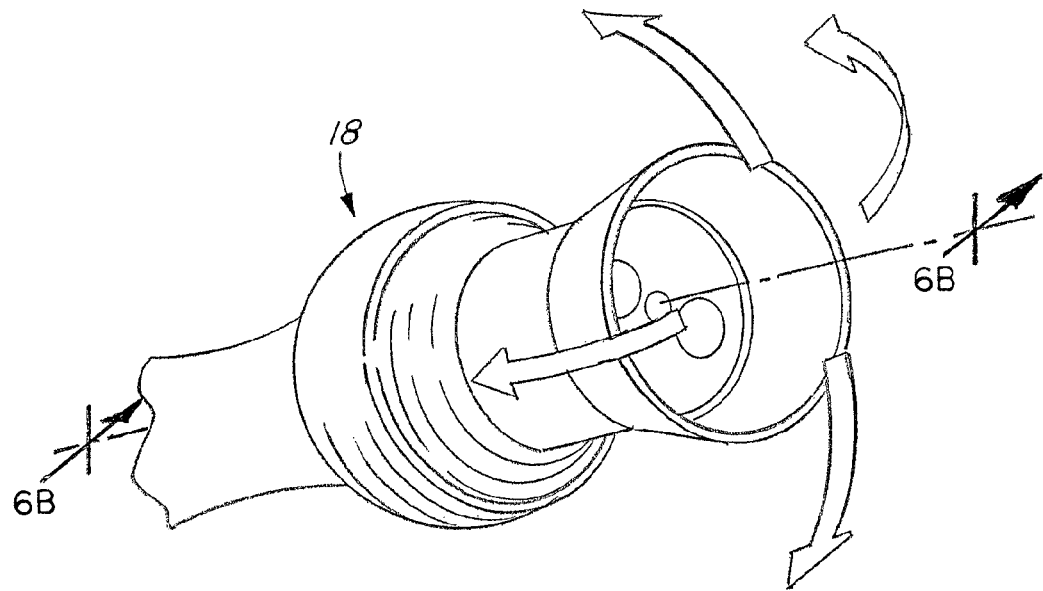
FIG. 6A is an enlarged perspective view of the actuator with the imaging device of the system for visualization of eye anatomy of FIG. 1.
Figure 6B:
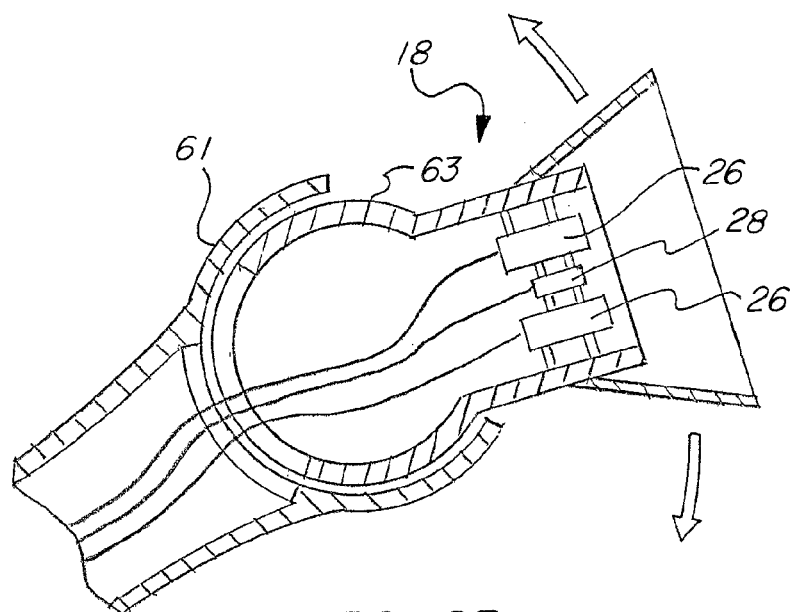
FIG. 6B is a cross-sectional view of the actuator of FIG. 6A, taken along the line "6B-6B".

Referring back to FIG. 1, the system (10) further includes an actuator (18) coupled to the imaging device (16) for moving the imaging device in different directions. In the exemplary embodiment shown in FIGS. 6A and 6B, the actuator (18) is a ball-socket type of the actuator including a socket part (61) and a ball part (63) that rotates inside the socket part, which enables rotary movement of the imaging device (16) in all directions. This, in turn, allows the cameras (26) to capture a wide angle of view of the eye anatomy, and in particular, the eye retina. The actuation of the actuator (18) is controlled via a controller (53) coupled to the device, or may be actuated manually by adjusting the position of the cameras in front of the person's eyes. The controller (53) is connected to the actuator (18) via a cable connection (51) or a wireless connection (55), which is particularly advantageous when the device is actuated by the physician positioned remotely from the patient. The housing (12) is also configured to facilitate translational movement of the imaging device (16), such that the cameras (26), in addition to being pivoted, can also be translated side to side or up and down.

In additional advantageous embodiments, the imaging device (16) includes a steerable flexible distal tip that can be translated linearly and rotationally to provide a wide angle view of the eye. For example, the imaging device shaft can include a plurality of steering lumens extending through the shaft and a center lumen for accommodating components of the imaging device. The steering lumens can be integrally formed as part of the shaft and radially offset from the longitudinal axis of the sheath and the center lumen. It is understood that any other suitable configuration and/or construction of the shaft and the steerable lumens may be used in accordance with the invention. The distal end of the imaging device (16) is actuated by engaging pull wire(s) disposed in each of the steering lumens. In other embodiments, any one or more of the steering lumens may be filled with pressured air in various amounts. In yet further embodiments, the opposite steering lumen(s) may be deflated with vacuum to facilitate the movement of the distal tip of the imaging device.

The distal end of the imaging device (16) can also be articulated by simply manually rotating the imaging device shaft via a proximal end of the shaft. Preferably, the shaft has enough stiffness to provide sufficient torque to allow for rotation of the distal end via the manual articulation of the proximal end.

Figure 4A:
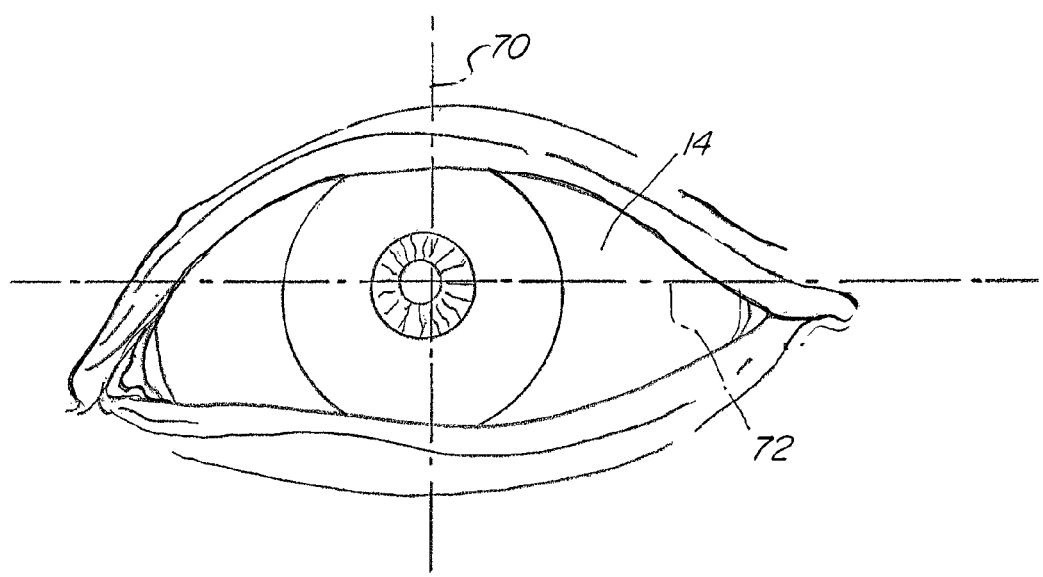
FIG. 4A is a schematic front view of a person's eye.

The imaging device (16) can be moved from a first position, in which the camera has a view vector along a first axis, to a second position, in which the camera has a view vector along a second axis that is offset from the first axis, as further discussed below in reference to FIGS. 4A-4E. The actuator (18) is capable of moving the cameras in a direction substantially parallel to at least one of a horizontal axis (72) of the eye (14) and a vertical axis (70) of the eye (14), as shown in FIG. 4A. Movement of the camera from the first position to the second position allows the physician to obtain an increased field of view of the patient's eye, and in particular, the patient's retina. In advantageous embodiments, this increased field of view is at least 180 degrees. In some cases, the total, combined field of view is 200 degrees or more.

Figure 4B:
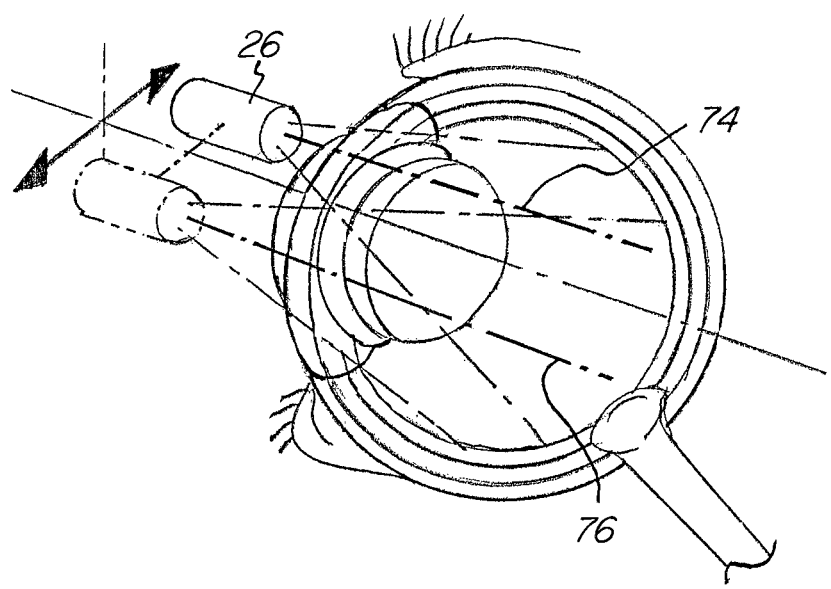
FIGS. 4B-E are partially isometric and schematic views of the camera of FIGS. 2A and 2B moving relative to the eye.

As shown in FIG. 4B, the camera (26) moves from a first position having a view vector along the first axis (74) to a second position having a view vector along a second axis (76), wherein the second axis (76) is substantially parallel to the first axis (74). This motion can be side to side, as depicted in FIG. 4B, the motion can also be up and down, as depicted in FIG. 4D, such that the camera (26) similarly moves from a first position having a view vector along first axis (78) to a second position having a view vector along second axis (80), wherein second axis (80) is substantially parallel to first axis (78). These motions can occur whether the camera (26) itself is pointed straight ahead or is pivoted at an angle.

Figure 4C:
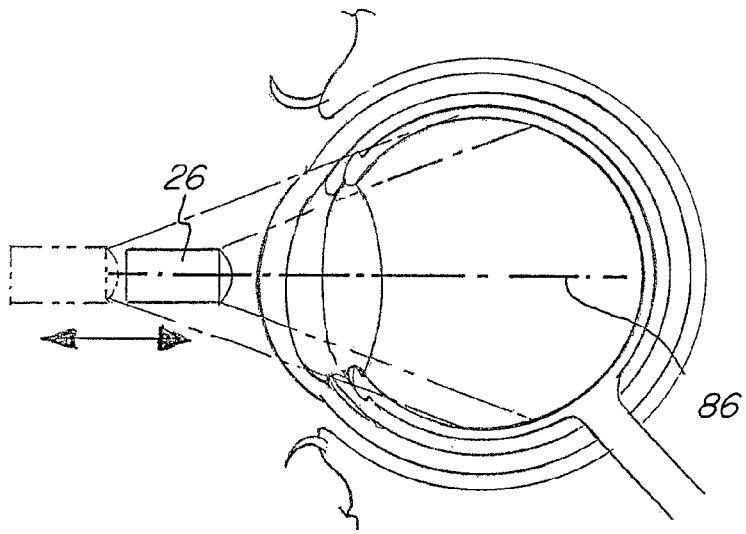
Figure 4D:
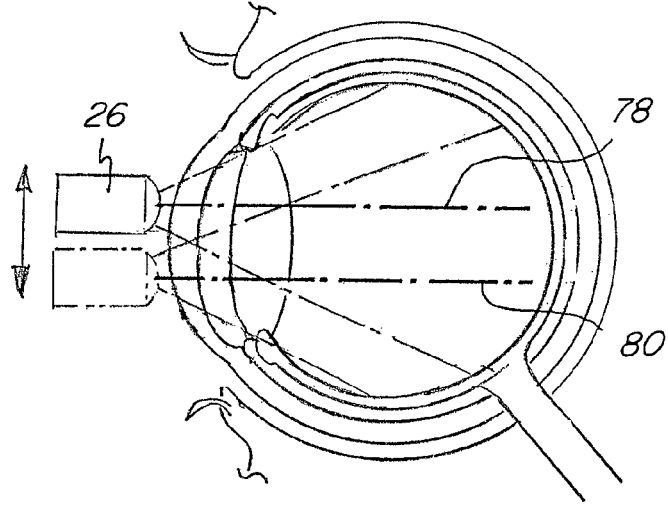
Figure 4E:
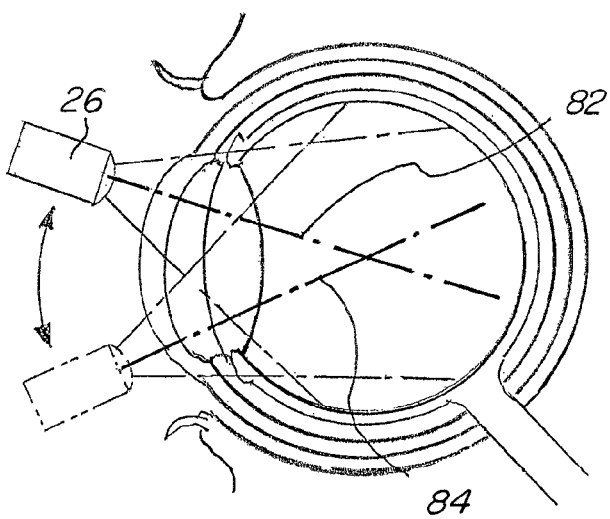

As shown in FIG. 4E, the camera (26) can also be moved from a first position having a view vector along a first axis (82) to a second position having a view vector along a second axis (84), wherein the second axis (84) is angularly offset from the first axis (82).

As shown in FIG. 4C, in additional advantageous embodiments, the actuator (18) is also capable of positioning the cameras (26) at a desired distance from the eye. In these embodiments, the cameras move (26) from the first position to a third position, in which the cameras have a view vector along the same axis (86) as when the cameras are in the first position.

It should be noted that, while only certain movements of the cameras (26) are described when discussing the illustrations of particular embodiments, any combination of the camera movements described in FIGS. 4A-4E, including all such movements, can be implemented in any individual embodiment by combining the various actuators described herein. It should also be noted that, in any of the embodiments described herein, the camera(s) adjacent one eye may be moved together with or separately from the camera(s) adjacent the other eye. Likewise, in any of the embodiments described herein, the camera(s) adjacent a single eye may be moved together as a unit or separately.

Figure 5A:
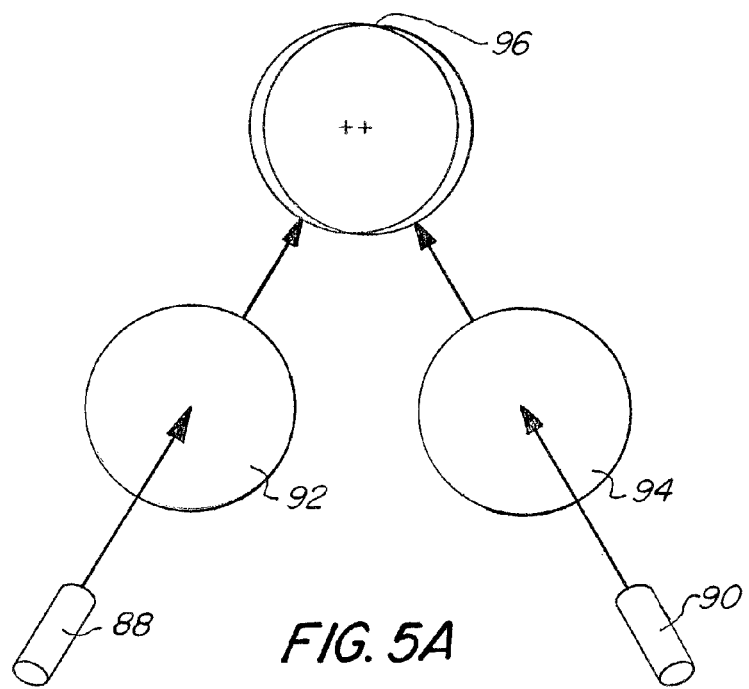
FIGS. 5A-5C are schematic views of different types of images captured by the camera used in the system of FIG. 1.

In some advantageous embodiments, one or more mosaic cameras are used to capture an image of the eye anatomy. The mosaic cameras have the structure described above or any other suitable structure. Each camera (88, 90) captures an image (92, 94) of the eye anatomy. The captured images are then sent to the processor, which processes the image data and displays the image to the user on a display. The images (92, 94) from each camera are laid over one another to produce a single image (96), as shown in FIG. 5A, which is displayed to the user. This allows the user to see an image of the eye anatomy having different depths and/or 3D characteristics.

Figure 5B:
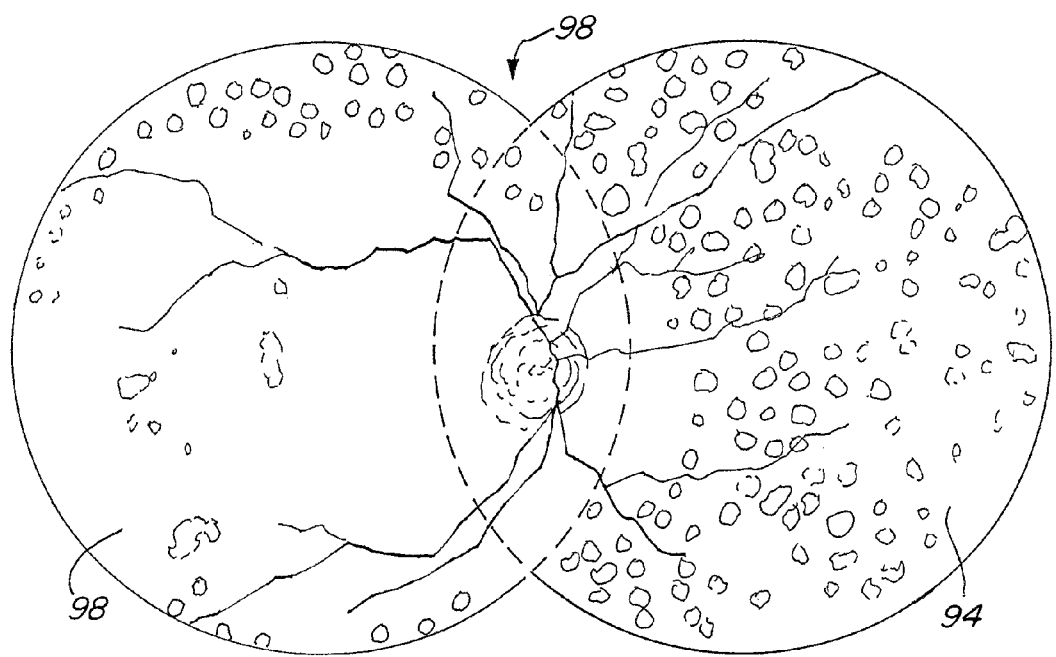

In additional embodiments, images captured by two or more cameras are "stitched" together when displayed to the user to provide for a more detailed image of the eye anatomy. For example, as shown in FIG. 5B, a first image (92) captured by a first camera and a second image (94) captured by a second camera are "stitched" or merged together to provide a single image (98), which is then displayed to the physician. This image (98) provides a much wider and detailed field of view of the eye anatomy as compared to a single camera image. It is understood that the images (92, 94) may be captured by the same camera positioned at different angles and/or distances from the eye, and then the images are combined to produce a stitched image.

Figure 5C:
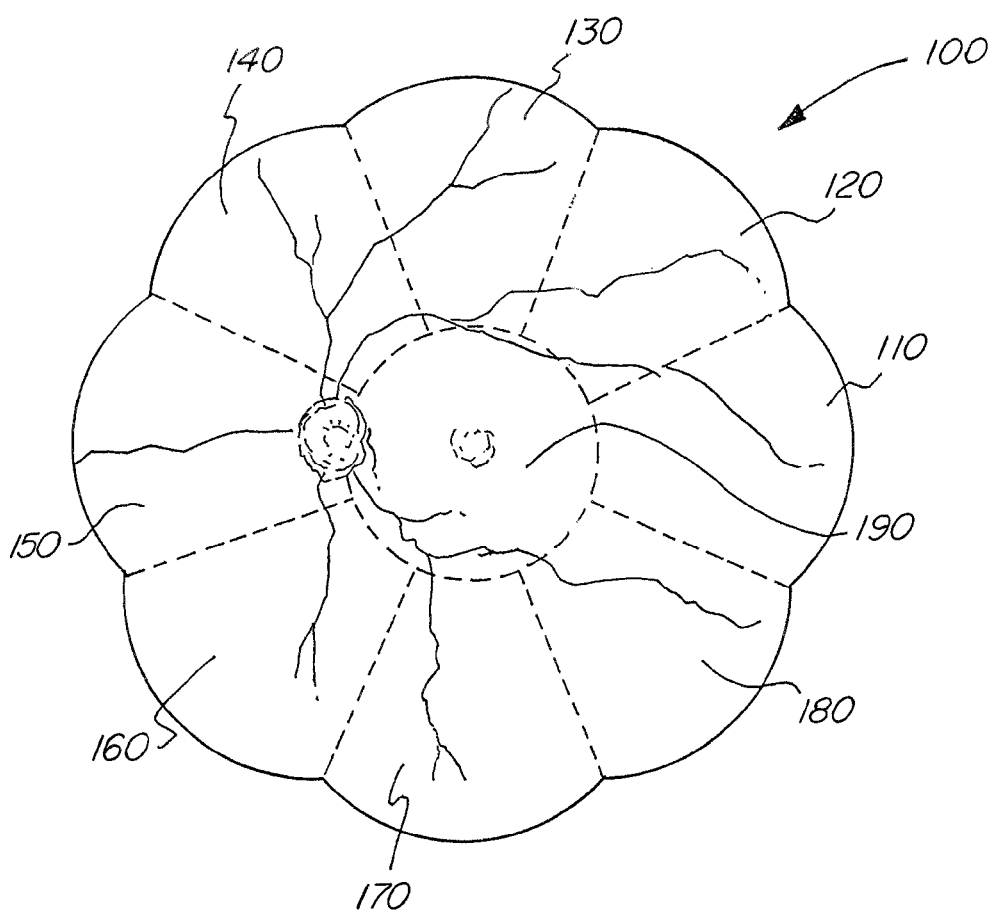

As shown in FIG. 5C, the composite image (100) displayed to the user may comprise multiple image segments "stitched" together, in this case nine image segments (110, 120, 130, 140, 150, 160, 170, 180, 190). In some embodiments, each of the nine image segments is captured by a separate camera. In other embodiments, the image segments are captured by a single camera or by any desired number of cameras. Once the captured image data is sent to the processor, the image segments are combined into one composite image to provide a larger picture of the eye anatomy and allow the physicians to view more surface area of the eye. The increased viewing area of the eye is essential for identifying and diagnosing various eye conditions.

Two or more cameras (26) may also be used to "scan" the eye. In some embodiments, two cameras are used wherein each camera is positioned at a different angle towards the eye. The cameras may start in a position wherein their view vectors overlap inside the eye, such as shown in FIG. 4E, and then move outwards such that the view vectors of each camera move away from each other, or diverging. This will provide an initial overlapping image and a series of subsequent images capturing the anatomy of the outer edges of the eye, which can then be combined or "stitched" together to provide a detailed composite image of the eye. In other embodiments, the two cameras start in a position where their view vectors are directed away from each other and then move towards each other until their view vectors overlap, or converge.

In another advantageous embodiment of the present invention, stereo camera is used to visualize the eye anatomy. The stereo camera includes two or more lenses, each with a separate image sensor. This allows the camera to simulate human binocular vision, making it possible to capture three-dimension images. The two or more image sensors are CMOS type sensors or any other suitable sensors, used together with one or more illumination sources. Each of the sensors captures an image from a different angle/position with respect to the eye. Then, the images are processed and displayed to the user as a single 3D image.

Referring back to FIG. 1, the system (10) further includes a processor (46) coupled to the imaging device (16) for receiving and processing image data captured by the cameras. Any suitable processor may be used in accordance with the present invention. For example, the processor (46) may be a personal computer. The digital image data captured by the imaging sensor positioned on the cameras (26) is transmitted to the processor for analysis and for creating images that are displayed to the physician. One of the techniques that are may be utilized to process the captured digital data is spectroscopy, which analyzes interaction between matter and radiated energy. By utilizing spectroscopy techniques, it is possible to digitally process spectrums and wavelengths reflected from the eye to detect and characterize various elements present in the eye.

In one advantageous embodiment, the processor (46) is connected to the cameras (26) via a cable or wired connection (48). In additional advantageous embodiments, the processor (46) is connected to the cameras (26) via a wireless, e.g. cellular or satellite, connection (50), which is desirable if a physician is located remotely from a patient, whose eye anatomy is being examined. For example, the system of the present invention may be used by physicians located in field conditions, such as on a battle field, wherein there is no time or accessibility to analyze the captured eye anatomy data. The physicians utilize the cameras to capture the image data and then send it wirelessly to remote locations for analysis. In further advantageous embodiments, the captured image data may be stored in cloud storage, meaning that the digital data is stored in logical pools, with the physical storage typically spanning across multiple servers managed by a hosting company. This way, the data may be easily accessed from any location connected to the cloud storage, such as physicians' and patients' personal computers, tablets and smart phones.

Furthermore, the cameras (26) and/or the processor (46) may be connected to an external storage device, a removable storage device, and/or to an internet port via a wired or wireless connection. The image data captured by the cameras is stored on the storage device (52) and may be later retrieved by a user. In other advantageous embodiments, the processor (46) may have an internal storage device. Any suitable storage device may be used in accordance with the present invention.

In some embodiments, the image data is compressed before it is transmitted to the processor for processing or storage. In other words, the imaging data is encoded using fewer bits than the originally captured data to reduce resource usage, such as data storage space or transmission capacity. Once the compressed data is received by the processor, it is decompressed before it is displayed to the user to maintain the original quality of the captured images.

The system (10) may further include a display (54) coupled to the processor (46) via a cable connection (56) or via a wireless connection (58). The display (54) receives imaging data processed by the processor (46) and displays the image of the person's eye anatomy in 2-D format and 3-D format to a physician. Any suitable type of a display may be used in accordance with the present invention.

In one advantageous embodiment, such as shown in FIG. 1, the system (10) further includes a user interface (60) coupled to the processor (46). The user interface (60) may be a graphical user interface (GUI), a keyboard, or any other suitable device that allows a user to input information and commands. The user interface is connected to the processor via a cable connection (62) or via a wireless connection (64). In some embodiments, the user interface (60) is displayed on the display (54) as on overlay image.

The device of the present invention utilizes a tracking system to track the motion of the eye and within the eye to adjust the cameras (20) to always obtain a clear and accurate image of the eye anatomy. Two different types of the tracking system are used. A first tracking system utilizes one or more cameras that track the motion of the eyeball itself. In order words, when the patient moves hers/his eyeball to look in a different direction, the cameras automatically adjust to that movement. This is accomplished by locating and recording certain landmarks or biomarkers within the eye, such as, for example 3 o'clock and 5 o'clock positions of the pupil, and then tracking the movement of those landmarks or biomarkers to determine a new position. Any suitable tracking mechanism may be use to accomplish this step. Then, the cameras and/or the entire housing moves to adjust the position with respect to the eye. It is understood that any other suitable tracking points or landmarks within the eye may also be used in this system.

A second tracking system tracks any motion within the eye. For example, the system tracks dilation/contraction of an iris and/or pupil of the eye, or movement of protein or crystalline material or other structures within the eye. This is accomplished by focusing one or more cameras on a particular structure or tissue in the eye and then automatically adjusting the position of the cameras as the structures/tissues move within the eye to maintain a laser focus on moving structures and/or tissues. Again, any suitable tracking mechanism is used for this step. In advantageous embodiments, both the first and second tracking systems are used in combination to track movement of the eye and structures within the eye to obtain a clear and accurate image of the eye anatomy.

When in use, the housing (12) is positioned over the person's eye (14) via the guide member (24) and is brought into contact with the eye. A vacuum is supplied through the lumen (20) to the housing (12), causing the housing to attach to the eye. Next, the imaging device (16) is positioned in the housing (12) adjacent the eye (14). The distal end of the imaging device having the camera (26) is then rotated or moved as desired to provide a wide angle view of the eye anatomy. The captured image is then transmitted to the processor (46) and the display (54) for viewing by the physician. In some advantageous embodiments, the image data is stored on the storage device (52) for later retrieval.

In some advantageous embodiments, a diameter of the iris is measured via any suitable measurement device. Data about the measured diameter is transmitted to a processor to determine a target opening. Based on this data, the processor then sends information to the controller for controlling actuation of the cameras to obtain wide angle view images of the eye anatomy.

It should be understood that the foregoing is illustrative and not limiting, and that obvious modifications may be made by those skilled in the art without departing from the spirit of the invention.

What is claimed is:

1. A system for visualization of eye anatomy, comprising:
   at least one camera having a view vector along a first axis when in a first position;
   a housing within which the at least one camera is housed, wherein said housing is configured and is movable to engage an eye of a patient such that said at least one camera is positioned adjacent the eye; and
   an actuator that moves said at least one camera from the first position to a second position;
   wherein said at least one camera, when in the second position, has a view vector along a second axis that is offset from the first axis; and
   wherein said at least one camera comprises a plurality of cameras positioned adjacent the same eye of the patient, and wherein each of said plurality of cameras moves separately from the other cameras.

2. The system of claim 1, wherein said housing comprises a suction member for attachment to the patient's eye.

3. The system of claim 1, further comprising a vacuum source that supplies vacuum to said housing to assist in attachment of said housing to the patient's eye.

4. The system of claim 1, wherein the second axis is angularly offset from the first axis.

5. The system of claim 1, wherein the second axis is substantially parallel to the first axis.

6. The system of claim 1, further comprising a processor that processes image data captured by said at least one camera.

7. The system of claim 1, further comprising at least one illumination device positioned adjacent said at least one camera.

8. The system of claim 7, wherein the at least one illumination device comprises a light source having at least one of a visible, ultraviolet, infrared and near infrared spectrum.

9. The system of claim 1, further comprising a storage device that stores image data captured by said at least one camera.

10. The system of claim 1, further comprising a 2-D or 3-D display coupled to said at least one camera for displaying image data captured by the camera.

11. The system of claim 1, wherein said actuator moves said at least one camera from the first position to a third position, wherein said camera has a view vector along the first axis when in the third position.

12. The system of claim 1, wherein said at least one camera captures a field of view of at least 180 degrees when moved from the first position to the second position.

13. The system of claim 1, wherein said at least one camera comprises at least one lens and at least one imaging sensor.

14. The system of claim 13, wherein said imaging sensor comprises a CMOS sensor.

15. The system of claim 1, further comprising a tracking system configured to track movement of the eye.

16. The system of claim 1, further comprising a tracking system configured to track movement of at least one structure and/or material within the eye.

17. A method of visualization of eye anatomy, comprising the steps of:
moving a housing within which at least one camera is housed toward a patient's eye to engage the patient's eye such that said at least one camera is positioned adjacent to the patient's eye, wherein said at least one camera has a view vector along a first axis when in a first position; and
moving said at least one camera to a second position;
wherein said at least one camera, when in the second position, has a view vector along a second axis that is offset from the first axis; and
wherein said at least one camera comprises a plurality of cameras positioned adjacent the same eye of the patient, and wherein the step of moving said at least one camera comprises moving each of said plurality of cameras separately from the other cameras.

18. The method of claim 17, wherein the step of engaging the patient's eye with the housing comprises engaging the patient's eye with a suction member provided in the housing.

19. The method of claim 17, wherein the step of engaging the patient's eye with the housing comprises supplying vacuum to the housing via a vacuum source connected to the housing to assist in attachment of the housing to the patient's eye.

20. The method of claim 17, further comprising the step of capturing image data with said at least one camera.

21. The method of claim 17, wherein the second axis is angularly offset from the first axis.

22. The method of claim 17, wherein the second axis is substantially parallel to the first axis.

23. The method of claim 17, further comprising the step of storing image data captured by said at least one camera on a storage device.

24. The method of claim 17, further comprising the step of displaying to a user image data captured by said at least one camera.

25. The method of claim 24, wherein the image data displayed to the user is an image comprising two or more images captured by said at least one camera, wherein two or more images are at least partially overlapping to create the displayed image.

26. The method of claim 17, further comprising the step of transmitting image data captured by said at least one camera to a remote location for display to a user and/or storage.

27. The method of claim 17, further comprising the step of illuminating the eye via at least one illumination device positioned adjacent said at least one camera.

28. The method of claim 17, further comprising the step of moving said at least one camera from the first position to a third position, wherein said camera has a view vector along the first axis when in the third position.

29. The method of claim 17, further comprising the step of measuring a diameter of an iris and adjusting the position of said at least one camera based at least in part on the measured diameter.

30. The method of claim 17, further comprising the step of tracking movement of the eye and adjusting positioning of said at least one camera based on the movement of the eye.

31. The method of claim 17, further comprising the step of tracking movement of at least one structure and/or material within the eye and adjusting positioning of said at least one camera based on the movement of the at least one structure and/or material within the eye.

* * * * *